(12) United States Patent  
Messerschmidt

(10) Patent No.: US 9,157,804 B2  
(45) Date of Patent: Oct. 13, 2015

(54) CORRELATION INTERFEROMETRIC METHODS, DEVICES AND SYSTEMS FOR LOW COST AND RUGGED SPECTROSCOPY

(75) Inventor: Robert G. Messerschmidt, Los Altos, CA (US)

(73) Assignee: Rare Light, Inc., Mountain View, CA (US)

( * ) Notice: Subject to any disclaimer, the term of this patent is extended or adjusted under 35 U.S.C. 154(b) by 436 days.

(21) Appl. No.: 13/145,699

(22) PCT Filed: Jan. 21, 2010

(86) PCT No.: PCT/US2010/021646  
§ 371 (c)(1),  
(2), (4) Date: Oct. 24, 2011

(87) PCT Pub. No.: WO2010/090872  
PCT Pub. Date: Aug. 12, 2010

(65) Prior Publication Data  
US 2012/0026483 A1  Feb. 2, 2012

Related U.S. Application Data

(60) Provisional application No. 61/146,166, filed on Jan. 21, 2009.

(51) Int. Cl.  
*G01J 3/453* (2006.01)  
*G01J 3/457* (2006.01)  
(Continued)

(52) U.S. Cl.  
CPC .............. *G01J 3/4531* (2013.01); *G01J 3/457* (2013.01); *G01N 21/45* (2013.01); *G01N 21/552* (2013.01); *G01N 21/65* (2013.01)

(58) Field of Classification Search  
CPC ............ A61B 8/06; A61B 8/08; A61B 8/488; G01B 9/02091; G01J 3/4531; G01J 3/457; G01N 21/65; G01N 21/552; G01N 21/45  
USPC .................... 356/300–334, 450–521  
See application file for complete search history.

(56) References Cited

U.S. PATENT DOCUMENTS

| 5,455,673 A | 10/1995 | Alsmeyer et al. |
| 5,652,653 A | 7/1997 | Alsmeyer |

(Continued)

FOREIGN PATENT DOCUMENTS

| EP | 0822395 A2 | 2/1998 |
| EP | 1630547 | 3/2006 |

(Continued)

OTHER PUBLICATIONS

"International Application Serial No. PCT/US2010/021646, Search Report mailed Aug. 31, 2010", 3 pgs.

(Continued)

*Primary Examiner* — Tarifur Chowdhury  
*Assistant Examiner* — Michael P Lapage  
(74) *Attorney, Agent, or Firm* — Schwegman Lundberg & Woessner, P.A.

(57) ABSTRACT

A correlation interferometric spectroscopy devices are described that detect the spectral characteristics of a sample wherein device consists of an electromagnetic radiation source for exciting a sample with photons; and a detector adapted to detect an arrival time of a photon at the detector and further adapted to detect a delay between the arrival time of different photons. The device may further consist of an autocorrelator adapted to analyze the between the arrival of photons at the detector. The device may also be used together with other spectral detection and characterizing systems, such as Raman spectroscopy and attenuated total reflectance spectroscopy. Also provided herein are methods, systems, and kits incorporating the correlation interferometric spectroscopy device.

46 Claims, 7 Drawing Sheets

(51) Int. Cl.
  *G01N 21/45* (2006.01)
  *G01N 21/552* (2014.01)
  *G01N 21/65* (2006.01)

(56) References Cited

U.S. PATENT DOCUMENTS

| | | | |
|---|---|---|---|
| 5,949,532 A | 9/1999 | Schrof et al. | |
| 6,141,100 A | 10/2000 | Burka et al. | |
| 7,876,869 B1* | 1/2011 | Gupta | 375/350 |
| 2003/0206297 A1* | 11/2003 | Barbieri et al. | 356/318 |
| 2006/0164633 A1 | 7/2006 | Koshoubu et al. | |
| 2008/0088795 A1* | 4/2008 | Goldstein et al. | 351/206 |
| 2009/0024360 A1* | 1/2009 | Arnvidarson | 702/189 |
| 2009/0316159 A1* | 12/2009 | Scott | 356/454 |
| 2010/0110423 A1* | 5/2010 | Villaumie | 356/301 |

FOREIGN PATENT DOCUMENTS

| | | | |
|---|---|---|---|
| EP | 1630547 A1 | 3/2006 | |
| JP | 56022939 * | 3/1981 | G01N 21/65 |
| JP | 10-501333 A | 2/1998 | |
| JP | 2001194305 A | 7/2001 | |
| WO | WO-00/66985 A1 | 11/2000 | |
| WO | WO-2007/001367 A2 | 1/2007 | |
| WO | WO-2007/112449 A2 | 10/2007 | |
| WO | WO-2008/086191 A1 | 7/2008 | |
| WO | WO-2010090872 A3 | 11/2010 | |

OTHER PUBLICATIONS

"International Application Serial No. PCT/US2010/021646, Written Opinion mailed Aug. 31, 2010", 5 pgs.

Dertinger, Thomas, et al., "Two-focus fluorescence correlation spectroscopy: a new tool for accurate and absolute diffusion measurements.", Chemphyschem., 8(3), (Feb. 19, 2007), 433-43.

Xu, Xiaoji G, et al., "Noise autocorrelation spectroscopy with coherent Raman scattering", Nature Physics, 4(2), (Feb. 2008), 125-129.

"Chinese Application Serial No. 201080013123.9, Office Action mailed May 27, 2013", (w/ English Translation), 15 pgs.

"European Application Serial No. 10738950.4, Office Action mailed Oct. 17, 2011", 2 pgs.

"European Application Serial No. 10738950.4, Response filed Apr. 24, 2012 to Office Action mailed Oct. 17, 2011", 3 pgs.

"International Application Serial No. PCT/US2010/021646, International Preliminary Report on Patentability mailed Aug. 4, 2011", 7 pgs.

"Korean Application Serial No. 10-2011-7019502, Office Action mailed May 28, 2013", (w/ English Translation), 3 pgs.

"Korean Application Serial No. 10-2011-7019502, Office Action mailed Aug. 30, 2012", (w/ English Translation), 23 pgs.

"Korean Application Serial No. 10-2011-7019502, Response filed Jul. 29, 2013 to Office Action mailed May 28, 2013", (w/ English Translation of Amended Claims), 14 pgs.

"Korean Applciation Serial No. 10-2011-7019502, Response filed Dec. 27, 2012 to Office Action mailed Aug. 30, 2012", 22 pgs.

"Chinese Application Serial No. 201080013123,9, Office Action mailed Jan. 13, 2014", (w/ English Translation), 10 pgs.

"Chinese Application Serial No. 201080013123.9, Response filed Mar. 28, 2014 to Office Action mailed Jan. 13, 2014", (w/ English Translation of Amended Claims), 14 pgs.

"Chinese Application Serial No. 201080013123.9, Response filed Oct. 11, 2013 to Office Action mailed May 27, 2013", (w/ English Translation of Amended Claims), 20 pgs.

"European Application Serial No. 10738950.4, Extended European Search Report mailed Oct. 23, 2013", 7 pgs.

Enderlein, Jorg, et al., "Using fluorescence lifetime for discriminating detector afterpulsing in fluorescence-correlation spectroscopy", *Review of Scientific Instruments*, 76(3), (2005), 033102-1-033102-5.

Laurence, T. A., et al., "Fast, flexible algorithm for calculating photon correlations", *Optics Letters*, 31(6), (Mar. 15, 2006), 829-831.

"Chinese Application Serial No. 201080013123.9, Office Action mailed Jul. 3, 2014", (w/ English Translation), 10 pgs.

"Chinese Application Serial No. 201080013123.9, Response filed Sep. 18, 2014 to Office Action mailed Jul. 3, 2014", (w/ English Translation of Claims), 17 pgs.

"Korean Application Serial No. 10.2012.7033951, Office Action mailed Feb. 25, 2015", w/ English Claims, 8 pgs.

"Korean Application Serial No. 10.2012.7033951, Response filed Apr. 27, 2015 to Office Action mailed Feb. 25, 2015", w/ English Claims, 15 pgs.

* cited by examiner

CORRELATION INTERFEROMETRIC METHODS, DEVICES AND SYSTEMS FOR LOW COST AND RUGGED SPECTROSCOPY

CROSS-REFERENCE TO CLAIM OF PRIORITY

This patent application is a U.S. National Stage filing under 35 U.S.C. 371 from International Patent Application Serial No. PCT/US2010/021646, filed Jan. 21, 2010 and published on Aug. 12, 2010 as WO 2010/090872 A2, which claims the priority benefit of U.S. Provisional Application No. 61/146,166 filed Jan. 21, 2009, the contents of which are incorporated herein by reference in their entirety.

FIELD OF THE INVENTION

The measurement of optical wavelength electromagnetic correlations can be made electronically as well as optically, by measuring delays between the arrivals of photons at very fast detectors. This field of study is known as correlation interferometry, and is the subject of this disclosure.

BACKGROUND OF THE INVENTION

Interferometers, as used in spectroscopy, are instruments that require a high degree of precision in manufacture. They must be assembled and maintained with accuracies of a small fraction of a wavelength. While such tolerances are routine in optomechanics today, it is expensive to build an instrument that requires such tight tolerance, especially if one or more components must move while holding this accuracy, as is the case with a scanning Michelson or Fabry-Perot interferometer. In the Michelson interferometer (or any two-beam interferometer) the delay between photons is changed by scanning a moving mirror in one leg of the interferometer. In correlation interferometry, the delay between two correlated photons is measured directly with very fast electronics.

Other concepts relating to correlation interferometer spectroscopy and interferometric spectroscopy in general are disclosed in, U.S. Pat. No. 6,504,614 to Messerschmidt et al. for Interferometer Spectrometer with Reduced Alignment Sensitivity; U.S. Pat. No. 7,324,210 to De Groot for Scanning Interferometry for Thin Film Thickness and Surface Measurements; U.S. Pat. No. 7,321,431 to De Groot for Method and System for Analyzing Low-Coherence Interferometry Signals for Information about Thin Film Structures; U.S. Pat. No. 7,315,382 to De Groot for Interferometry Method for Ellipsometry, Reflectometry, and Scatterometry Measurements, including Characterization of Thin Film; U.S. Pat. No. 7,304,745 to Towers et al. for Phase Measuring Method and Apparatus for Multi-Frequency Interferometry; U.S. Pat. No. 7,280,224 to Hill et al. for Interferometry Systems and Methods of Using Interferometry Systems; U.S. Pat. No. 7,280,223 to Hill et al. for Interferometry Systems and Methods of Using Interferometry Systems; U.S. Pat. No. 7,251,041 to Hill for Spatial Filtering in Interferometry; U.S. Pat. No. 7,139,081 to De Groot et al for Interferometry Method for Ellipsometry, Refectometry, and Scatterometry Measurements, including Characterization of Thin Film Structures; US 2007/0103694 to Kato for Interferometry System; US 2001/0042831 to Wood et al. for Photon Detector; US 2007/0041011 to Hayden et al. for Fast Time-Correlated Multi-Element Photon Detector and Method; US 2004/0178348 to Wainer et al. for Pixelated Photon Detector.

One way to overcome the intricacies of interferometers is to make the precision components "solid state" or "monolithic." If this can be achieved, an instrument with such components will be more rugged. For example, to achieve this, Fabry-Perot interferometers sometimes have novel scanning mechanisms. One scanning or tuning approach is to vary the refractive index of the material in the interferometer cavity. This has been done both with liquid crystal materials, and by changing the pressure of a gas in the cavity. Another way to overcome this dilemma is to eliminate the use of optics entirely. Correlation phenomena happen routinely, as light waves of sufficient coherence interact with each other. No special optical instruments are really needed to detect these effects. In any interference spectroscopy, the delay between two photon paths must be measured or varied. Table 1 lists the measurements that can be made, and how those measurements can be used or applied.

TABLE 1

| MEASURED PARAMETER | DERIVED PARAMETER | APPLICATIONS |
| --- | --- | --- |
| Fringe Position | Mean phase difference | Length standards Length comparison Machine control Refractometry velocity of light |
|  | Phase variations | Microtopography Optical testing |
| Fringe Visibility | Spectrum source | Profile of symmetrical lines |
|  | Spatial distribution at source | Stellar diameters |
| Full Intensity Distribution (position and visibility) | Spectrum of Source | Direct interference spectroscopy Fourier spectroscopy |
|  | Spatial distribution at source | Optical transfer function hologram |

Given this background, there exists a need for a correlation interferometric spectroscopy system that eliminates the need for precision optical components all-together in the attainment of spectra through a process of interference.

SUMMARY OF THE INVENTION

An aspect of the invention is directed toward a correlation interferometric spectroscopy device for detecting the spectral characteristics of a sample. The device comprises an electromagnetic radiation source for exciting a sample with photons; and a detector adapted to detect an arrival time of a photon at the detector and further adapted to detect a delay between the arrival times of different photons. Additionally, the device can further comprise an autocorrelator for analyzing the delay between photon arrivals at the detector. For, example the analysis of arrival times of the photons can be measured and analyzed using an aliasing method. Additionally, the correlation interferometric spectroscopy device can be used together with other spectroscopy methods, such as Raman spectroscopy, attenuated total reflectance spectroscopy, and/or pericritical reflectance spectroscopy. Alternatively, the correlation interferometric spectrometer can be used with a source doubling interferometer, such as a Lloyd's Mirror arrangement, where correlation spectroscopy is used to measure the delay between photons.

A method for determining the spectral properties of a sample is also provided herein. The method comprises the steps of emitting electromagnetic radiation from an electromagnetic radiation source; irradiating the sample with the electromagnetic radiation source, wherein photons from the electromagnetic radiation source interact with the sample; and detecting arrival times of photons at a detector, wherein the photons are exiting the sample. Additionally, the method can further include the step of analyzing the arrival times of the photons exiting the sample.

Another aspect of the invention is directed to a system for detecting the spectral properties of a sample. The system comprises an electromagnetic radiation source for exciting a sample with photons; and a detector adapted to detect an arrival time of a photon at the detector and further adapted to detect a delay between the arrival times of different photons.

A kit for detecting the spectral properties of a sample is also provided. The kit includes, for example, an electromagnetic radiation source for emitting electromagnetic radiation; and a detector adapted to detecting photon arrival and further adapted to detect a delay between the arrivals of photons. Additionally the kit can further comprise an autocorrelator for analyzing the delay between photon arrivals.

An aspect of the disclosure is directed to correlation interferometric spectroscopy devices. The devices comprise: at least one electromagnetic radiation source for exciting a sample with photons; and one or more detectors adapted to detect an arrival time of a photon at the one or more detectors and further adapted to detect a delay between the arrival time of different photons. Additionally, an autocorrelator can be provided that is adapted to analyze the delay between photon arrival. Moreover, correlations between photons can be measured using an aliaser. Additionally, a Raman spectroscopy device, a peri-critical reflection spectroscopy device, and/or an attenuated total reflectance spectroscopy device can be used with the interferometric spectroscopy devices. In some configurations a system clock adapted and configured to associate a time with an emission of an electromagnetic radiation from a source. The system clock can be adapted and configured to associate a time with a detection of an electromagnetic radiation from a sample. A power source is also provided. In some configurations a communicator adapted and configured to communicate a measurement from at least one of the one or more detectors, an autocorrelator, a computer processing unit, a delay link, and a memory. One or more components of the device can be configured in a housing wherein one or more of the components are removeable (e.g., power source).

Another aspect is directed to a method for determining the spectral properties of a sample. The method comprises the steps of: emitting electromagnetic radiation from an electromagnetic radiation source; irradiating the sample with the electromagnetic radiation source, wherein photons from the electromagnetic radiation source interact with the sample; and detecting an arrival time of a photons at a detector, wherein the photons are exiting the sample. The method can also further comprise the step of analyzing arrival times of photons exiting the sample.

In yet another aspect, systems are provided which are adapted and configured to detect spectral properties of a sample. The systems comprise: an electromagnetic radiation source for exciting a sample with photons; and a detector adapted to detect an arrival time of a photon at the detector and further adapted to detect a delay between the arrival time of different photons. Additionally, an autocorrelator can be provided that is adapted to analyze the delay between photon arrival. Moreover, correlations between photons can be measured using an aliaser. Additionally, a Raman spectroscopy device, a peri-critical reflection spectroscopy device, and/or an attenuated total reflectance spectroscopy device can be used with the interferometric spectroscopy devices. In some configurations a system clock adapted and configured to associate a time with an emission of an electromagnetic radiation from a source. The system clock can be adapted and configured to associate a time with an detection of an electromagnetic radiation from a sample. A power source is also provided. In some configurations a communicator adapted and configured to communicate a measurement from at least one of the one or more detectors, an autocorrelator, a computer processing unit, a delay link, and a memory. One or more components of the device can be configured in a housing wherein one or more of the components are removeable (e.g., power source).

In still other aspects, kits are provided for detecting the spectral properties of a sample. The kits comprise: an electromagnetic radiation source for emitting electromagnetic radiation; and a detector adapted to detecting photon arrivals and further adapted to detect a delay between the arrival of photons. Additional kit components include an autocorrelator adapted to analyze the delay between photon arrivals.

Other aspects include one or more networked apparatuses. The networked apparatuses comprise: a memory; a processor; a communicator; a display; and a correlation interferometric spectroscopy device comprising at least one electromagnetic radiation source for exciting a sample with photons, and one or more detectors adapted to detect an arrival time of a photon at the one or more detectors and further adapted to detect a delay between the arrival time of different photons.

In some aspects communication systems are provided. The communication systems comprise: a system for detecting a characteristic of a sample comprising a correlation interferometric spectroscopy device comprising at least one electromagnetic radiation source for exciting a sample with photons, and one or more detectors adapted to detect an arrival time of a photon at the one or more detectors and further adapted to detect a delay between the arrival time of different photons; a server computer system; a measurement module on the server computer system for permitting the transmission of a sample measurement from the system for measuring the characteristic of the sample over a network; at least one of an API engine connected to at least one of the system for measuring the characteristic of the sample to create a message about the sample measurement and transmit the message over an API integrated network to a recipient having a predetermined recipient user name, an SMS engine connected to at least one of the system for measuring the characteristic of the sample to create an SMS message about the sample measurement and transmit the SMS message over a network to a recipient device having a predetermined sample measurement recipient telephone number, and an email engine connected to at least one of the system for measuring the characteristic of the sample to create an email message about the sample measurement and transmit the email message over the network to a sample measurement recipient email having a predetermined sample measurement recipient email address. A storing module can also be provided on the server computer system for storing the sample measurement on the system for measuring the characteristic of the sample server database. Moreover, at least one of the system for measuring the characteristic of the sample is connectable to the server computer system over at least one of a mobile phone network and an Internet network, and a browser on the sample measurement recipient electronic device is used to retrieve an interface on the server computer system. Additionally, a plurality of email addresses are held in a system for measuring the characteristic of the sample database and fewer than all the email addresses are individually selectable from the computer system, the email message being transmitted to at least one sample measurement recipient email having at least one selected email address. In some instances at least one of the system for measuring the characteristic of the sample is connectable to the server computer system over the Internet, and a browser on the sample measurement recipient electronic device is used to retrieve an interface on the server computer system. Where the system is in communication with, for example, a healthcare provider a plurality of user names are held in the system for detecting spectral characteristics database and fewer than all the user names are individually selectable from the computer system, the message being transmitted to at least one sample measurement recipient user name via an API. The sample measurement recipient electronic device can also be connectable to the server computer system over the Internet, and a browser on the sample measurement recipient electronic device is used to retrieve an interface on the server computer system. The sample measurement recipient electronic device may also be connected to the server computer system over a cellular phone network, such as where the electronic device is a mobile device. Additionally, the system can include an interface on the server computer system, the interface being retrievable by an application on the sample measurement recipient mobile device. In some cases, the SMS sample measurement is received by a message application on the sample measurement recipient mobile device. Where a plurality of SMS sample measurements are received for the sample measurement, each by a respective message application on a respective sample measurement recipient mobile device. At least one SMS engine can be configured to receive an SMS response over the cellular phone SMS network from the sample measurement recipient mobile device and stores an SMS response on the server computer system. Additionally, a sample measurement recipient phone number ID is transmitted with the SMS sample measurement to the SMS engine and is used by the server computer system to associate the SMS sample measurement with the SMS response. Moreover, the server computer system can be connectable over a cellular phone network to receive a response from the sample measurement recipient mobile device. The SMS sample measurement can also include a URL that is selectable at the sample measurement recipient mobile device to respond from the sample measurement recipient mobile device to the server computer system, the server computer system utilizing the URL to associate the response with the SMS sample measurement. The communication system can further comprise in at least some configurations: a downloadable application residing on the sample measurement recipient mobile device, the downloadable application transmitting the response and a sample measurement recipient phone number ID over the cellular phone network to the server computer system, the server computer system utilizing the sample measurement recipient phone number ID to associate the response with the SMS sample measurement. In other configurations, the system can comprise: a transmissions module that transmits the sample measurement over a network other than the cellular phone SMS network to a sample measurement recipient user computer system, in parallel with the sample measurement that is sent over the cellular phone SMS network, and/or a downloadable application residing on the sample measurement recipient host computer, the downloadable application transmitting a response and a sample measurement recipient phone number ID over the cellular phone network to the server computer system, the server computer system utilizing the sample measurement recipient phone number ID to associate the response with the SMS sample measurement.

INCOPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Low cost, rugged correlation interferometric spectroscopy systems and apparatuses could be useful in a wide-variety of applications. For example, interferometric spectroscopy systems can be used in: non-invasive medical measurements, including the measurement of glucose and other bodily analyte levels in the body by means of fluorescence, photoacoustic, near-infrared, Raman, terahertz, or mid-infrared spectroscopy; quantitative measurements of analytes of medical interest in tissue; imaging of body components such as heart valves and anastomoses using chemical functional group imaging; and measurement of blood gas parameters non-invasively using spectroscopy. Additionally, correlation interferometric spectroscopy systems and apparatuses can be further combined with attenuated total reflectance (ATR) techniques near the critical angle. Application of the disclosure can further be used in industrial process measurements which require low-cost, rugged, and possibly disposable sensors. Correlation interferometric spectroscopy systems and apparatuses can be useful for measurements of tissue optical properties for the purpose of identification of individuals, as in biometric applications. The devices, systems, methods and kits described herein combine the use of correlation interferometry with the measurement of optical spectra in situations where it is necessary to produce spectral measurements at low cost and in a very rugged fashion.

I. Spectroscopy Devices

Figure 1A:
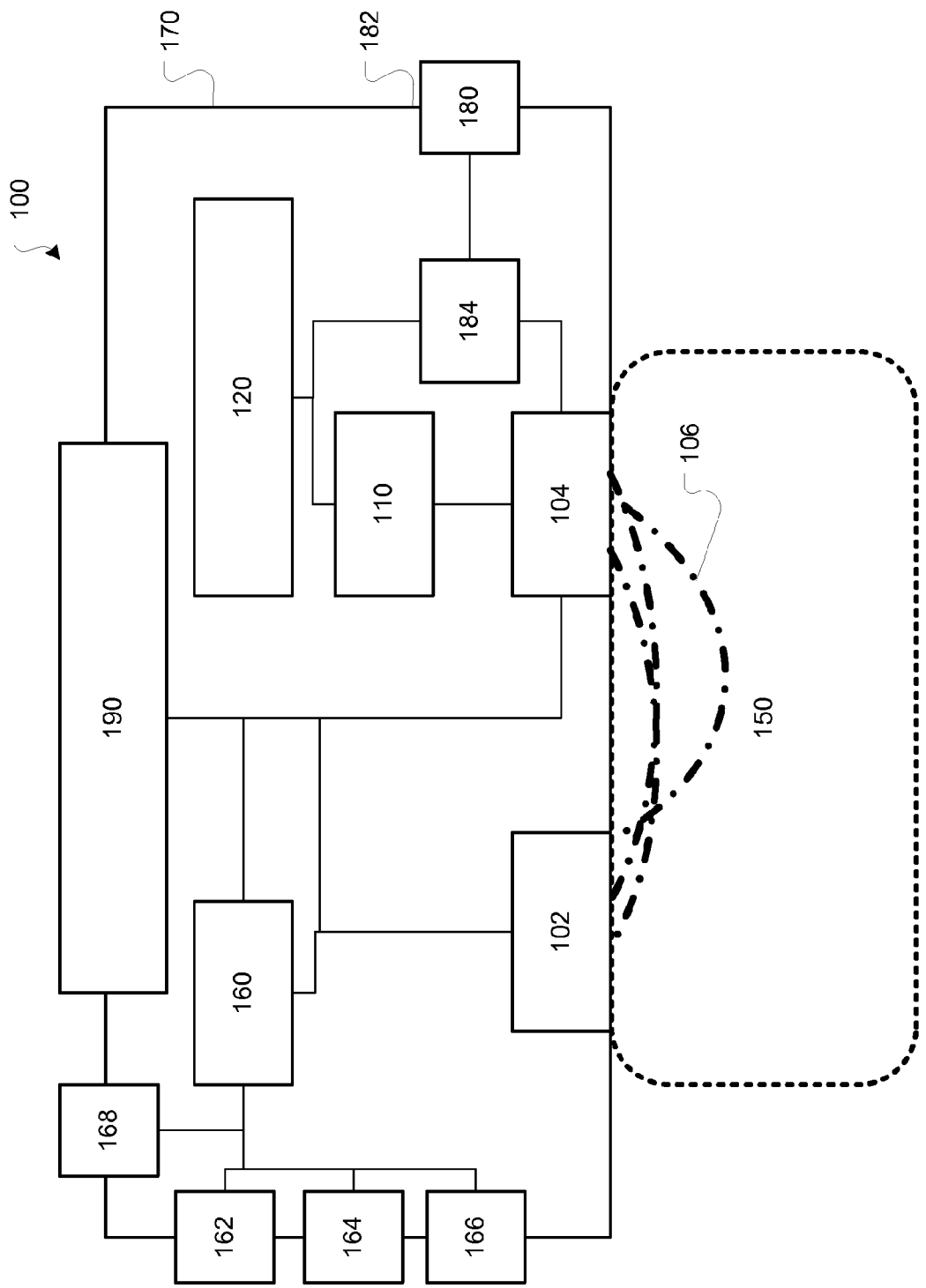
FIG. 1A is diagram from a side perspective of a correlation interferometric spectroscopy device having a single emitter and a single detector.
Figure 1B:
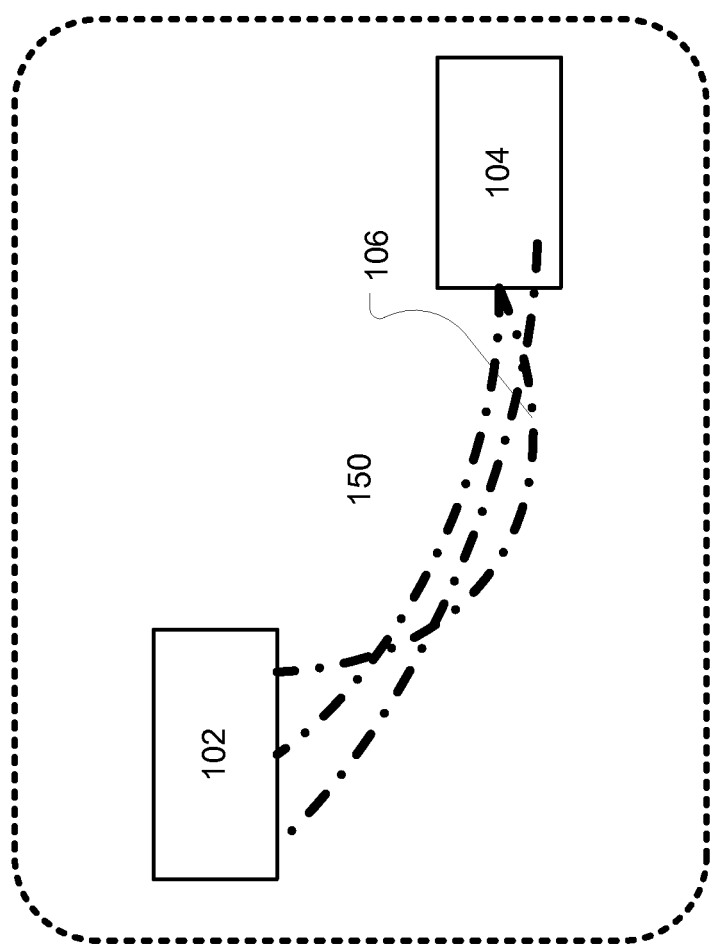
FIG. 1B is diagram from a top perspective of a correlation interferometric spectroscopy device as shown in FIG. 1A.

A correlation interference spectroscopy device 100 is shown in FIG. 1A from a side view and a top view in FIG. 1B. In a correlation spectroscopy device 100, a source of radiation from an electromagnetic (EM) radiation source is introduced from an EM emitter 102 to a sample 150. The electromagnetic radiation from the EM emitter 102 can, for example, be a laser or a light emitting diodes (LEDs), or any other suitable electromagnetic radiation source (for example, LumiLEDS LXHL-FH3C, available from Philips Lumileds, San Jose, Calif.). Photons from the electromagnetic radiation enter into the sample 150 and interact with the molecules comprising the sample. Photons 106 from the EM emitter 102 pass through the sample and are transformed to contain absorption information about the sample through which the photons passed. As these photons migrate through and exit the sample, the photons may also interact with each other if the photons are separated spatially and temporally by less than the coherence interval. This interaction results in fringes which contain frequency (wavelength) information. The delay between photon arrival may be measured either directly or by inspecting the electric signal derived from the radiation.

A plurality of photons 106 (with each photon path illustrated as a separate line) generated by the EM emitter passes through the sample 150 before detection by EM detector 104. A correlation interference spectroscopy system, which may be detected by a system consisting of multiple detectors, can also be used. One or more detectors 104 can be placed near each other or, alternatively, the detectors can be placed at different distances with respect to the source of radiation. A single detector may be used as is shown in FIGS. 1A-B. When a single detector 104 is used, the delay is measured by looking for autocorrelations in the fluctuating signal as different delay lines 110 are added. Delay lines can be switched electronically or swapped out while the device is in operation, or at another time (e.g., during a pre-deployment configuration step), as will be appreciated by those skilled in the art. As contemplated herein, the one or more delay lines 110 used by Mandel are replaced with solid state circuitry to measure autocorrelation. Additionally, in the correlation interferometric spectroscopy system described herein, there are no optics or moving parts, as shown in FIGS. 1A-B. As previously noted, although FIGS. 1A-B illustrates only one detector, more than one detector may be implemented in the design. In some configurations the detector is further connected to an autocorrelator 120 which analyzes the delay between photons received by the detector 104.

Typically, correlation interferometry spectroscopy requires very fast detectors. The faster the detector, the broader the free spectral range. The free spectral range for the measurement is given by equation (1):

$$\Delta\nu = 1/2\delta\tau \quad (1)$$

Because of the fast times required for correlation interferometer spectroscopy, a typical photomultiplier tube is not sufficient to serve as a detector since a photomultiplier tube can not distinguish times shorter than $\delta\tau \sim 10{-8}$ s. Any autocorrelation functions are typically sampled at intervals greater than this. For example, for a system operating at the near infrared region at 2000 nm, the free spectral range (FSR) would be $10^{-4}$ nm with a photomultiplier operating at 100 MHz. In order to obtain a FSR of 100 nm, the detector must operate at 6 orders of magnitude faster, or 100 THz. Fast detectors for detecting photons include Silicon photomultipliers (SiPM), superconducting single photon detectors, or any other suitable photon detector.

In some cases, the devices, systems and methods takes advantage of aliasing. Aliasing refers to the distortion that occurs when a continuous time signal has frequencies larger than half of the sampling rate. Aliasing can cause the components of the signal at high frequencies to be mistaken for components at lower frequencies. Therefore, if the detector is not fast enough, this is equivalent to undersampling in time in an interferometer. The spectral information is still present, but it is aliased to a lower (false) frequency.

Correlation interferometry typically does not extract any information about the phase of the coherence between the photons. It only extracts information about the modulus of the correlation. Spectral distributions can therefore only be found from the measurements if some assumptions are made. This is the same situation Michelson faced in deriving the profiles of spectral lines from the visibility by assuming the lines to be symmetrical. The minimum requirement for quantitative spectroscopy is two wavelengths at least one of which is in the vicinity of an absorption band. This basic requirement is met with correlation interferometry, even with a very limited free spectral range. A measurement of the ratio of the two ends of the free spectral range can be made, or the area under the curve can be calculated. This is proportional to the concentration of the species responsible for the absorption band. The device can be configured such that it is contained within a suitable housing 170. In another configuration, the components can be configured such that the components function as a housing. In still other configurations, the components are modularizable such that one or more components can be positioned within a housing that is in communication with a second housing containing one or more other components.

Additionally, the devices can be provided with a central processing unit (CPU) 160 adapted and configured to control the operation of the device and associated components of the device, one or more displays 164 (such as liquid crystal display (LCD)) to provide immediate visual feedback of the data reading to a user, audio capability (such as a speaker) 162 to enable the results to be provided audibly, one or more memory devices 180 (e.g., read only memory to control operation and write memory to store data to enable multiple data results to be stored on the device), a data port 182 (such as a PCMCIA port or USB port) to enable retrieval of data, wireless data transmission capability to enable wireless transmission of data to a central system, on/off button(s) 168 to allow user activation of the device, and control buttons 166 to allow interface with, for example, the speaker and display.

Where the device is part of a system monitoring the measurements taken by the device (such as a communication network discussed more fully below), a system clock 184 can be provided which associates a date/time stamp with a data collection from one or more detectors 104.

The device can be powered by any suitable power source 190, including, for example, a removeable battery or a plug adapted to access an AC or DC power source.

Moreover, the components can be incorporated into, for example, a diagnostic device or system that is adapted and configured to perform diagnostic tests on a sample. Suitable devices include, for example, non-invasive glucose measuring devices, industrial biodiesel production reactors and fermentation bioreactors.

The devices, systems and methods disclosed herein can also be used together with Raman spectroscopy apparatuses, pericritical reflectance spectroscopy devices, and/or attenuated total reflectance (ATR) devices.

Suitable peri-critical reflectance spectroscopy apparatuses include those disclosed in PCT Publication WO 2009/137122 A2 entitled Methods, Devices and Kits for Peri-critical Reflectance Spectroscopy dated Nov. 12, 2009 (Messerschmidt).

A peri-critical reflectance spectroscopy apparatus or system, is adapted to provide a source of electromagnetic radiation which can be introduced into a sample. The electromagnetic radiation can be modulated, for example, by an interferometer prior to contacting the sample. The modulated radiation can also be focused by a lens onto a reflective surface, such as a mirror, which then reflects the light into an ATR prism. Furthermore, in some instances, the mirror can be adjusted so that the electromagnetic radiation is introduced to the sample through a range of angles which encompasses a target critical angle. In other words, the electromagnetic radiation is introduced at an angle less than the critical angle and is swept in increments through the critical angle to an angle greater than the critical angle. The mirror can be adjusted to change the angle at which the electromagnetic radiation enters the sample. Alternatively the electromagnetic radiation can be introduced directly to the ATR prism. The electromagnetic radiation, once inside the ATR prism then comes into contact with the sample. The electromagnetic radiation then exits the prism and is detected by a detector and processed by a data processing system.

The critical angle information obtained using the systems and devices described herein is another dimension of information, which is not now obtained with existing technology. A complete map of a sample would therefore be a full map of reflected light intensity versus wavelength versus a mapping of the angle of incidence, at angles that approach and then in fact somewhat cross over, the critical angle. An angular resolution of a few millidegrees (a few microradians) is necessary, because the depth of penetration is very sensitive to the angle of incidence around the critical angle. Additionally, a processor can be used with the apparatus to analyze the critical angle data. Once an angular map of the sample is generated by, for example, scanning the sample, the actual angle of the critical angle for the each wavelength can be determined A spectrum at each wavelength at a constant effective depth can then be plotted.

For a peri-critical reflectance spectroscopy apparatus, power source is provided that is adapted and configured to provide power to a source for electromagnetic radiation or light is adapted to deliver a light beam to an interferometer, which separates the beam of light into two or more beams, such as by means of reflection, and thereafter brings the rays together to produce interference. Suitable power sources include, but are not limited to, batteries. As will be appreciated by those skilled in the art, the system can be contained within a suitably designed housing or the components can be configured such that the components function as a housing. The resulting beam then passes through a lens, after which it comes in contact with a mirror. The mirror reflects the resultant beam through a prism and towards a sample. A reflected second beam passes back through the prism where it is received by a multi-element detector. The detector can be adapted and configured to resolve an angle of incidence for the pixels to achieve a resolution of a millidegree or better. The resolved pixels are then analyzed using a suitable data processing device or computer. The analysis can include, for example, comparing the data against a library of data to determine a variance of the detected signal to a known sample. Additionally, the system can include a display, such as a liquid crystal display (LCD), adapted to provide a display to a user of the full map of reflected light intensity versus wavelength versus a mapping of the angle of incidence. As will be appreciated by those skilled in the art, connectivity can also be provided which enables the system to sent the information to a printer, or a network. Connectivity can be, for example, wirelessly via the internet as well as via suitable connection ports.

The peri-critical reflectance spectroscopy apparatus or system can be set-up such that the electromagnetic radiation is introduced by a beam to a sample using a mirror, such as a tilt/shift mirror having a 0.001 degree resolution. The beam can be delivered to the sample after being passed through a spatial filter. Passing the beam through the filter can result in a beam divergence, typically 0.001 degree. After passing through the filter, the divergence beam comes in contact with a tilt shift mirror which deflects the beam through a peri-critical reflectance (PR) crystal into the sample. Suitable samples can, for example, have a same area as low as 1-10 mm in diameter. After the beam comes in contact with the same, a resulting beam is reflected. The resultant beam can then pass back through the PR crystal to contact a second tilt/shift mirror which transmits the resultant beam through a lens and into a small area single element mercury cadmium telluride (MCT) detector.

Suitable Raman spectroscopy apparatuses include those disclosed in PCT Patent Application No. PCT/US2010/21528 entitled RAMAN SPECTROSCOPY USING MULTIPLE DISCRETE LIGHT SOURCES, filed Jan. 20, 2010, and claiming priority to U.S. Provisional Patent Application 61/146,195 filed Jan. 21, 2009. If the device is used in a Raman spectroscopy system, silicon detectors can be used. Silicon detectors are fast yet are relatively low in cost. Also, when used with Raman spectroscopy, the apparatus described herein is more likely able to make a good quantitative measurement using only a small range of wavelengths, since fundamental vibrations can be looked at instead of overtones.

The Raman spectroscopy devices include, for example, a multiplicity of discrete light sources a source for Raman spectroscopy. An excitation source is a multiplicity of discrete light sources. The multiplicity of discrete light sources typically emits electromagnetic radiation over a range of ten to several hundred nanometers. This light is modulated into a series of wavelength-specific cosine waves by an interferometer, such as the Michelson interferometer. Alternatively, the sources may be self modulated. The device is powered by one or more suitable power sources. The power sources can be removable if desired. Suitable power sources include, but are not limited to batteries.

One or more lenses then focus the electromagnetic radiation onto the sample for high efficiency. When the electromagnetic radiation interacts with the sample, the electromagnetic radiation is then scattered due to the properties of a sample. The scattered radiation is collected by a collection lens. The collected radiation then passes through a narrow bandpass (NBP) filter. The wavelength of the NBP filter is selected so that it filters out the radiation that is within the bandpass of the input radiation. Having passed through the NBP filter, the electromagnetic radiation that arrives at the detector is of the same narrow wavelength and contains the modulation frequencies imparted by the Michelson interferometer or by the self-modulation of the light sources. The Raman intensities for each source of the electromagnetic radiation arriving at the detector are recovered by taking the Fourier transform of the signal arriving at the detector.

Although electromagnetic radiation of any wavelength region could be used, typically wavelengths in the green or red region of the spectrum are used. Red wavelengths usually considered ideal for biological applications, for two reasons. First, red is within the so-called "therapeutic window" which is a region of the spectrum that transmits well through human tissue. The therapeutic window is often stated to be from 600 to 900 nanometers. A narrow bandpass filter, is placed in front of the detector. The bandpass is just beyond the emitting region of any of the sources. For Stokes Raman, the narrow detector filter is to the longer wavelength (lower energy) side of the source region.

The multiplicity of modulated discrete light sources is typically a collection of discrete narrow band laser light sources. The bandwidth of the collection of sources will determine the range of analysis for the measurement, so a sufficient number of discrete sources are used in order to measure at all of the important spectral features in the system.

Figure 2A:
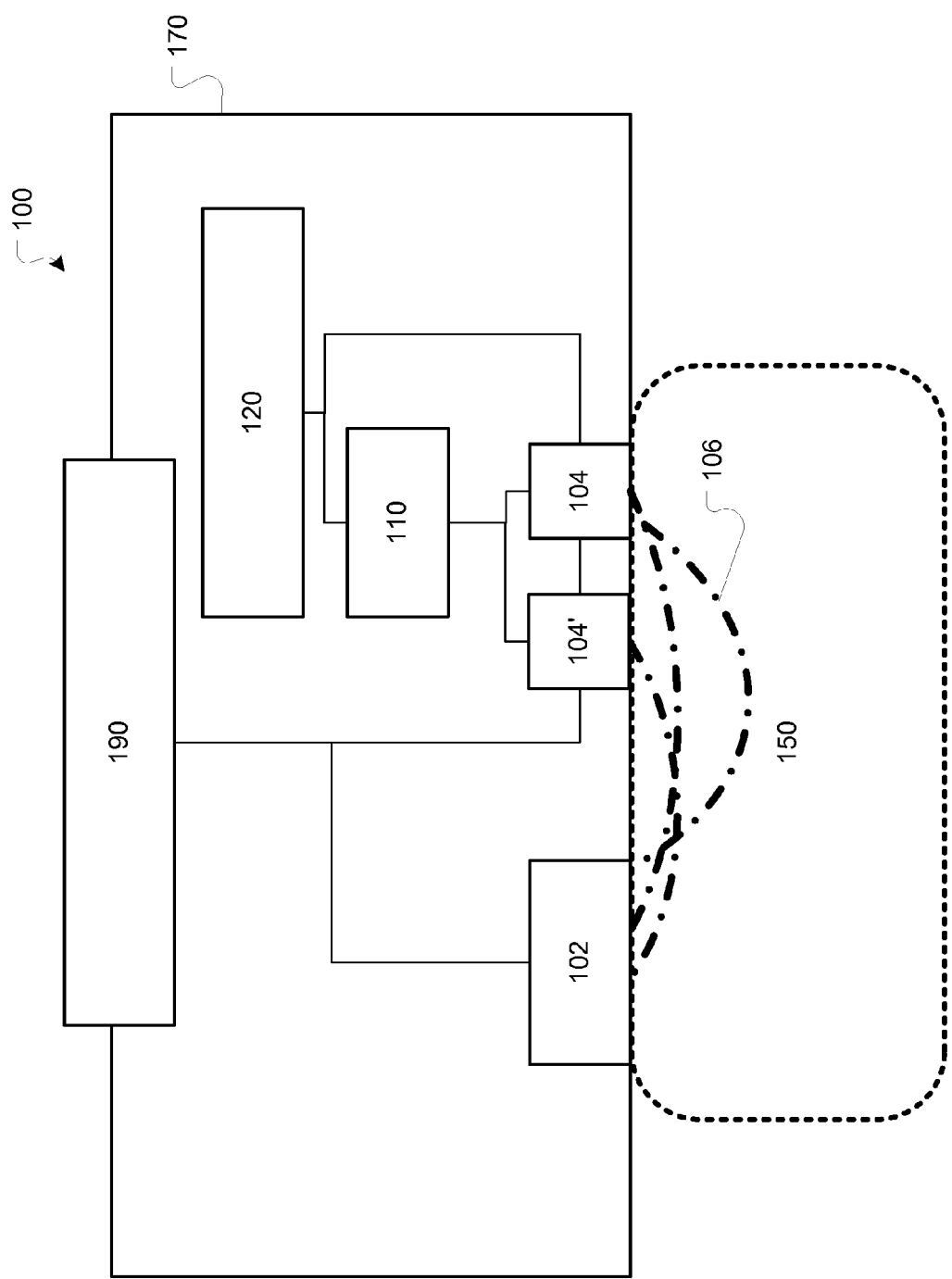
FIG. 2A is diagram from a side perspective of a correlation interferometric spectroscopy device having a single emitter and two detectors.
Figure 2B:
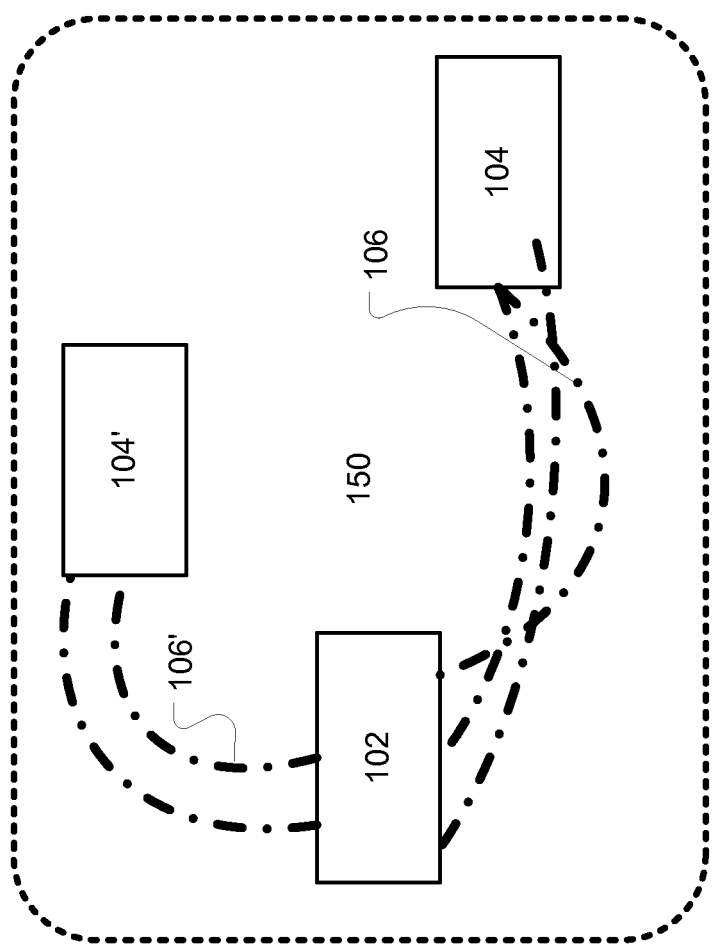
FIG. 2B is diagram from a top perspective of a correlation interferometric spectroscopy device as shown in FIG. 2A.

Turning back to the configuration of the correlation interferometric spectroscopy devices, in cases where two detectors 104, 104' are used, as shown in FIGS. 2A-B, the delay between photons arises in the same way as in classical interferometry. Each set of photons 106, 106' detected by the corresponding detectors 104, 104' are detected at different times based on the distance the detector is from the emitter and the path the photons have traveled through the sample 150. To avoid obscuring the figure, the additional components (memory, buttons, audio, etc.) shown in FIG. 1A are not reproduced in FIG. 2A.

II. Methods for Determining Spectral Properties of a Sample

Figure 3:
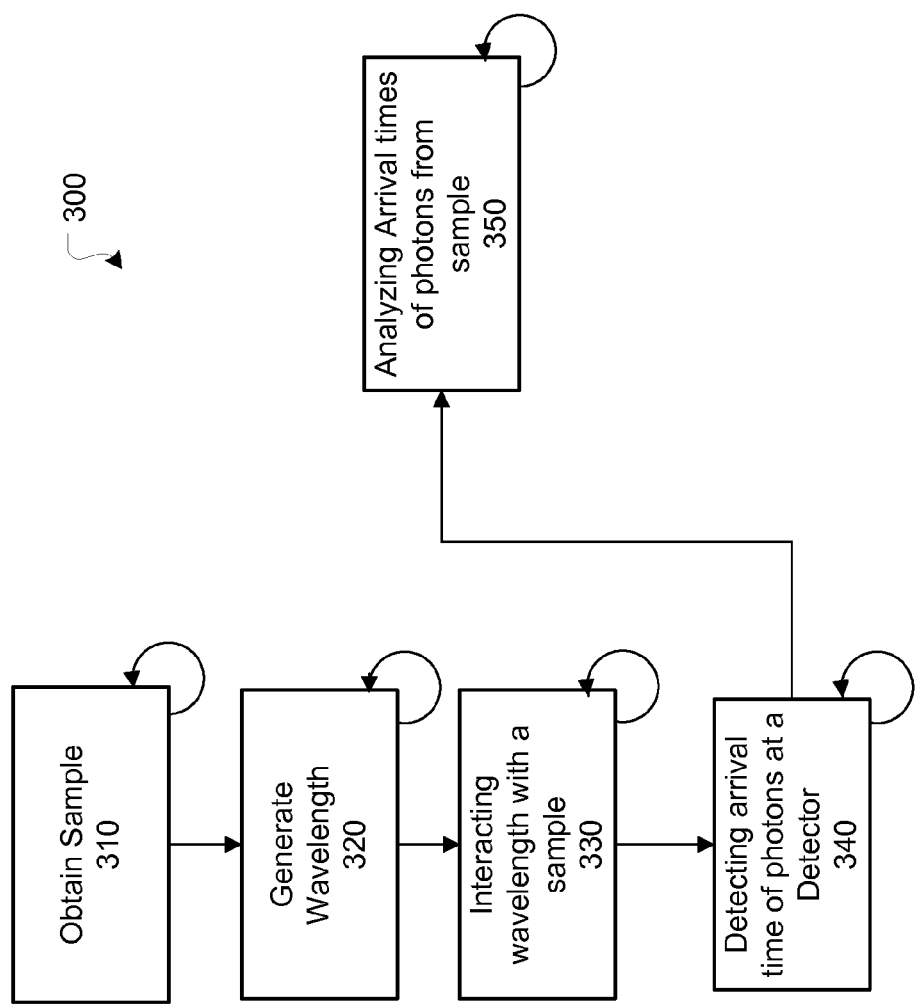
FIG. 3 is a flow chart illustrating methods of using a spectroscopy device.

As illustrated in FIG. 3, methods 300 are contemplated for determining spectral properties of a sample. The method includes emitting electromagnetic radiation from an electromagnetic radiation source 310, as described above, and irradiating a sample 320. The photons from the electromagnetic source interact with the sample 330. The photons continue to pass through a sample until the photons are detected by a detector 340. As the photons pass through the sample and interact with the sample, characteristics of the photons are altered. The detector detects arrival time of the photons at the detector 350 and then analyzes the difference in time from the photons entering the sample and exiting the sample.

As will be appreciated by those skilled in the art, the steps of obtaining or selecting a sample, generating a wavelength, interacting the wavelength with the sample, and detecting arrival time of the wavelength photons from the sample can be performed in a first location (e.g., in conjunction with patient monitoring) while the step of analyzing the arrival times of photons from the sample can be performed either at the first location or a second location (e.g., where the device is in communication with a central system). Samples upon which this method can be applied include, but are not limited to, skin, blood (and its constituents), and human tissue, as well as industrial processes such as biodiesel production and fermentation reaction.

III. Spectroscopy Devices and Communications Networks

As will be appreciated by those skilled in the art, modular and scalable system employing one or more of the spectroscopy devices discussed above can be provided which are comprised of a controller and more than one spectroscopy devices. Controller communicates with each spectroscopy device over a communication media. Communication media may be a wired point-to-point or multi-drop configuration. Examples of wired communication media include Ethernet, USB, and RS-232. Alternatively communication media may be wireless including radio frequency (RF) and optical. The spectroscopy device may have one or more slots for fluid processing devices. Networked devices can be particularly useful in some situations. For example, networked devices that provide blood glucose monitoring results to a care provider (such as a doctor) can facilitate background analysis of compliance of a diabetic with diet, medication and insulin regimes which could then trigger earlier intervention by a healthcare provider when results begin trending in a clinically undesirable direction. Additionally, automatic messages in response to sample measurements can be generated to either the patient monitoring their glucose level and/or to the care provider. In some instances, automatic messages may be generated by the system to either encourage behavior (e.g., a text message or email indicating a patient is on track) or discourage behavior (e.g., a text message or email indicating that sugars are trending upward). Other automated messages could be either email or text messages providing pointers and tips for managing blood sugar. The networked communication system therefore enables background health monitoring and early intervention which can be achieved at a low cost with the least burden to health care practitioners.

Figure 4A:
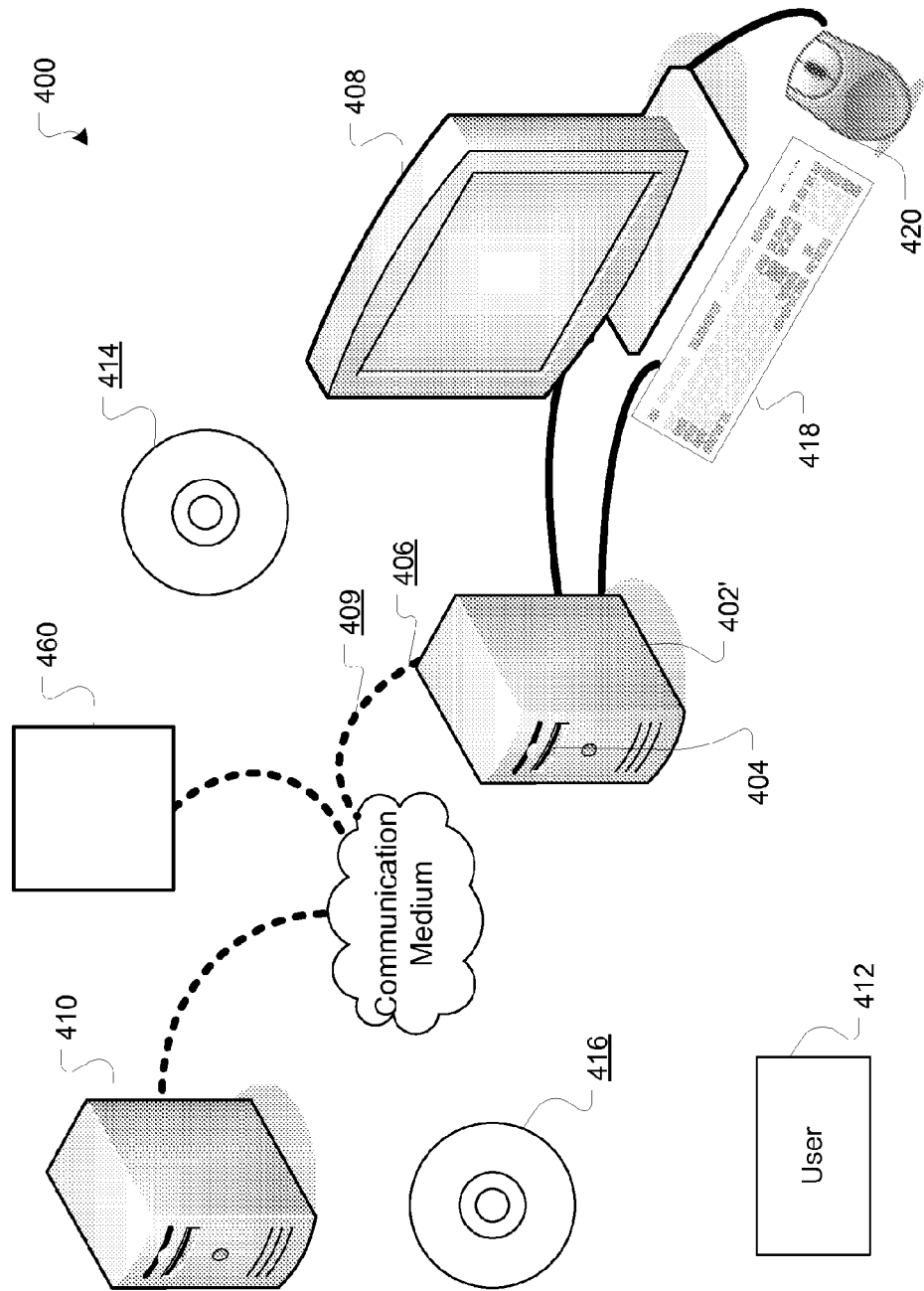
FIG. 4A is a block diagram showing a representative example of a logic device through which dynamic a modular and scalable system can be achieved.

To further appreciate the networked configurations of multiple spectroscopy device in a communication network, FIG. 4A is a block diagram showing a representative example logic device through which a browser can be accessed to control and/or communication with spectroscopy device described above. A computer system (or digital device) 400, which may be understood as a logic apparatus adapted and configured to read instructions from media 414 and/or network port 406, is connectable to a server 410, and has a fixed media 416. The computer system 400 can also be connected to the Internet or an intranet. The system includes central processing unit (CPU) 402, disk drives 404, optional input devices, illustrated as keyboard 418 and/or mouse 420 and optional monitor 408. Data communication can be achieved through, for example, communication medium 409 to a server 410 at a local or a remote location. The communication medium 409 can include any suitable means of transmitting and/or receiving data. For example, the communication medium can be a network connection, a wireless connection, or an internet connection. It is envisioned that data relating to the use, operation or function of the one or more spectroscopy device (shown together for purposes of illustration here as 460) can be transmitted over such networks or connections. The computer system can be adapted to communicate with a user (users include healthcare providers, physicians, lab technicians, nurses, nurse practitioners, patients, and any other person or entity which would have access to information generated by the system) and/or a device used by a user. The computer system is adaptable to communicate with other computers over the Internet, or with computers via a server. Moreover the system is configurable to activate one or more devices associated with the network (e.g., diagnostic devices and/or spectroscopy device) and to communicate status and/or results of tests performed by the devices and/or systems.

As is well understood by those skilled in the art, the Internet is a worldwide network of computer networks. Today, the Internet is a public and self-sustaining network that is available to many millions of users. The Internet uses a set of communication protocols called TCP/IP (i.e., Transmission Control Protocol/Internet Protocol) to connect hosts. The Internet has a communications infrastructure known as the Internet backbone. Access to the Internet backbone is largely controlled by Internet Service Providers (ISPs) that resell access to corporations and individuals.

The Internet Protocol (IP) enables data to be sent from one device (e.g., a phone, a Personal Digital Assistant (PDA), a computer, etc.) to another device on a network. There are a variety of versions of IP today, including, e.g., IPv4, IPv6, etc. Other IPs are no doubt available and will continue to become available in the future, any of which can, in a communication network adapted and configured to employ or communicate with one or more spectroscopy devices, be used without departing from the scope of the invention. Each host device on the network has at least one IP address that is its own unique identifier and acts as a connectionless protocol. The connection between end points during a communication is not continuous. When a user sends or receives data or messages, the data or messages are divided into components known as packets. Every packet is treated as an independent unit of data and routed to its final destination—but not necessarily via the same path.

The Open System Interconnection (OSI) model was established to standardize transmission between points over the Internet or other networks. The OSI model separates the communications processes between two points in a network into seven stacked layers, with each layer adding its own set of functions. Each device handles a message so that there is a downward flow through each layer at a sending end point and an upward flow through the layers at a receiving end point. The programming and/or hardware that provides the seven layers of function is typically a combination of device operating systems, application software, TCP/IP and/or other transport and network protocols, and other software and hardware.

Typically, the top four layers are used when a message passes from or to a user and the bottom three layers are used when a message passes through a device (e.g., an IP host device). An IP host is any device on the network that is capable of transmitting and receiving IP packets, such as a server, a router or a workstation. Messages destined for some other host are not passed up to the upper layers but are forwarded to the other host. The layers of the OSI model are listed below. Layer 7 (i.e., the application layer) is a layer at which, e.g., communication partners are identified, quality of service is identified, user authentication and privacy are considered, constraints on data syntax are identified, etc. Layer 6 (i.e., the presentation layer) is a layer that, e.g., converts incoming and outgoing data from one presentation format to another, etc. Layer 5 (i.e., the session layer) is a layer that, e.g., sets up, coordinates, and terminates conversations, exchanges and dialogs between the applications, etc. Layer-4 (i.e., the transport layer) is a layer that, e.g., manages end-to-end control and error-checking, etc. Layer-3 (i.e., the network layer) is a layer that, e.g., handles routing and forwarding, etc. Layer-2 (i.e., the data-link layer) is a layer that, e.g., provides synchronization for the physical level, does bit-stuffing and furnishes transmission protocol knowledge and management, etc. The Institute of Electrical and Electronics Engineers (IEEE) sub-divides the data-link layer into two further sub-layers, the MAC (Media Access Control) layer that controls the data transfer to and from the physical layer and the LLC (Logical Link Control) layer that interfaces with the network layer and interprets commands and performs error recovery. Layer 1 (i.e., the physical layer) is a layer that, e.g., conveys the bit stream through the network at the physical level. The IEEE sub-divides the physical layer into the PLCP (Physical Layer Convergence Procedure) sub-layer and the PMD (Physical Medium Dependent) sub-layer.

Wireless networks can incorporate a variety of types of mobile devices, such as, e.g., cellular and wireless telephones, PCs (personal computers), laptop computers, wearable computers, cordless phones, pagers, headsets, printers, PDAs, etc. and suitable for use in a system or communication network that includes one or more spectroscopy devices. For example, mobile devices may include digital systems to secure fast wireless transmissions of voice and/or data. Typical mobile devices include some or all of the following components: a transceiver (for example a transmitter and a receiver, including a single chip transceiver with an integrated transmitter, receiver and, if desired, other functions); an antenna; a processor; display; one or more audio transducers (for example, a speaker or a microphone as in devices for audio communications); electromagnetic data storage (such as ROM, RAM, digital data storage, etc., such as in devices where data processing is provided); memory; flash memory; and/or a full chip set or integrated circuit; interfaces (such as universal serial bus (USB), coder-decoder (CODEC), universal asynchronous receiver-transmitter (UART), phase-change memory (PCM), etc.). Other components can be provided without departing from the scope of the invention.

Wireless LANs (WLANs) in which a mobile user can connect to a local area network (LAN) through a wireless connection may be employed for wireless communications between one or more spectroscopy devices. Wireless communications can include communications that propagate via electromagnetic waves, such as light, infrared, radio, and microwave. There are a variety of WLAN standards that currently exist, such as Bluetooth®, IEEE 802.11, and the obsolete HomeRF.

By way of example, Bluetooth products may be used to provide links between mobile computers, mobile phones, portable handheld devices, personal digital assistants (PDAs), and other mobile devices and connectivity to the Internet. Bluetooth is a computing and telecommunications industry specification that details how mobile devices can easily interconnect with each other and with non-mobile devices using a short-range wireless connection. Bluetooth creates a digital wireless protocol to address end-user problems arising from the proliferation of various mobile devices that need to keep data synchronized and consistent from one device to another, thereby allowing equipment from different vendors to work seamlessly together.

An IEEE standard, IEEE 802.11, specifies technologies for wireless LANs and devices. Using 802.11, wireless networking may be accomplished with each single base station supporting several devices. In some examples, devices may come pre-equipped with wireless hardware or a user may install a separate piece of hardware, such as a card, that may include an antenna. By way of example, devices used in 802.11 typically include three notable elements, whether or not the device is an access point (AP), a mobile station (STA), a bridge, a personal computing memory card International Association (PCMCIA) card (or PC card) or another device: a radio transceiver; an antenna; and a MAC (Media Access Control) layer that controls packet flow between points in a network.

In addition, Multiple Interface Devices (MIDs) may be utilized in some wireless networks. MIDs may contain two independent network interfaces, such as a Bluetooth interface and an 802.11 interface, thus allowing the MID to participate on two separate networks as well as to interface with Bluetooth devices. The MID may have an IP address and a common IP (network) name associated with the IP address.

Wireless network devices may include, but are not limited to Bluetooth devices, WiMAX (Worldwide Interoperability for Microwave Access), Multiple Interface Devices (MIDs), 802.11x devices (IEEE 802.11 devices including, 802.11a, 802.11b and 802.11g devices), HomeRF (Home Radio Frequency) devices, Wi-Fi (Wireless Fidelity) devices, GPRS (General Packet Radio Service) devices, 3 G cellular devices, 2.5 G cellular devices, GSM (Global System for Mobile Communications) devices, EDGE (Enhanced Data for GSM Evolution) devices, TDMA type (Time Division Multiple Access) devices, or CDMA type (Code Division Multiple Access) devices, including CDMA2000. Each network device may contain addresses of varying types including but not limited to an IP address, a Bluetooth Device Address, a Bluetooth Common Name, a Bluetooth IP address, a Bluetooth IP Common Name, an 802.11 IP Address, an 802.11 IP common Name, or an IEEE MAC address.

Wireless networks can also involve methods and protocols found in, Mobile IP (Internet Protocol) systems, in PCS systems, and in other mobile network systems. With respect to Mobile IP, this involves a standard communications protocol created by the Internet Engineering Task Force (IETF). With Mobile IP, mobile device users can move across networks while maintaining their IP Address assigned once. See Request for Comments (RFC) 3344. NB: RFCs are formal documents of the Internet Engineering Task Force (IETF). Mobile IP enhances Internet Protocol (IP) and adds a mechanism to forward Internet traffic to mobile devices when connecting outside their home network. Mobile IP assigns each mobile node a home address on its home network and a care-of-address (CoA) that identifies the current location of the device within a network and its subnets. When a device is moved to a different network, it receives a new care-of address. A mobility agent on the home network can associate each home address with its care-of address. The mobile node can send the home agent a binding update each time it changes its care-of address using Internet Control Message Protocol (ICMP).

In basic IP routing (e.g., outside mobile IP), routing mechanisms rely on the assumptions that each network node always has a constant attachment point to the Internet and that each node's IP address identifies the network link it is attached to. Nodes include a connection point, which can include a redistribution point or an end point for data transmissions, and which can recognize, process and/or forward communications to other nodes. For example, Internet routers can look at an IP address prefix or the like identifying a device's network. Then, at a network level, routers can look at a set of bits identifying a particular subnet. Then, at a subnet level, routers can look at a set of bits identifying a particular device. With typical mobile IP communications, if a user disconnects a mobile device from the Internet and tries to reconnect it at a new subnet, then the device has to be reconfigured with a new IP address, a proper netmask and a default router. Otherwise, routing protocols would not be able to deliver the packets properly.

Figure 4B:
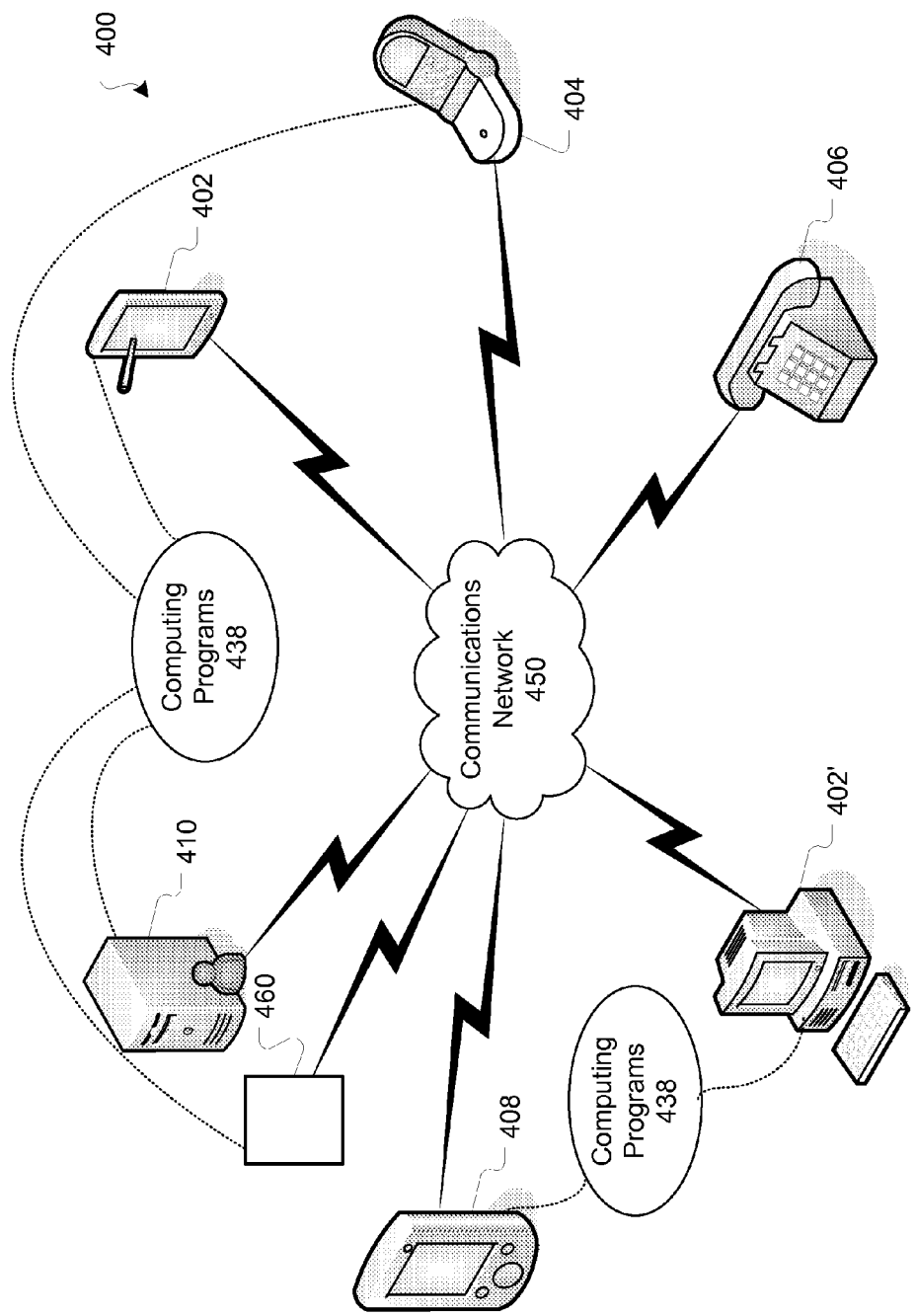
FIG. 4B is a block diagram showing the cooperation of exemplary components of a system suitable for use in a system where dynamic data analysis and modeling is achieved.

Computing system 400, described above, can be deployed as part of a computer network that includes one or devices 460, such as spectroscopy devices. In general, the description for computing environments applies to both server computers and client computers deployed in a network environment. FIG. 4B illustrates an exemplary illustrative networked computing environment 400, with a server in communication with client computers via a communications network 450. As shown in FIG. 4B, server 410 may be interconnected via a communications network 450 (which may be either of, or a combination of a fixed-wire or wireless LAN, WAN, intranet, extranet, peer-to-peer network, virtual private network, the Internet, or other communications network) with a number of client computing environments such as tablet personal computer 402, mobile telephone 404, telephone 406, personal computer 402', and personal digital assistant 408. In a network environment in which the communications network 450 is the Internet, for example, server 410 can be dedicated computing environment servers operable to process and communicate data to and from client computing environments via any of a number of known protocols, such as, hypertext transfer protocol (HTTP), file transfer protocol (FTP), simple object access protocol (SOAP), or wireless application protocol (WAP). Other wireless protocols can be used without departing from the scope of the invention, including, for example Wireless Markup Language (WML), DoCoMo i-mode (used, for example, in Japan) and XHTML Basic. Additionally, networked computing environment 400 can utilize various data security protocols such as secured socket layer (SSL) or pretty good privacy (PGP). Each client computing environment can be equipped with operating system 438 operable to support one or more computing applications, such as a web browser (not shown), or other graphical user interface (not shown), or a mobile desktop environment (not shown) to gain access to server computing environment 400.

In operation, a user (not shown) may interact with a computing application running on a client computing environment to obtain desired data and/or computing applications. The data and/or computing applications may be stored on server computing environment 400 and communicated to cooperating users through client computing environments over exemplary communications network 450. A participating user may request access to specific data and applications housed in whole or in part on server computing environment 400. These data may be communicated between client computing environments and server computing environments for processing and storage. Server computing environment 400 may host computing applications, processes and applets for the generation, authentication, encryption, and communication data and applications and may cooperate with other server computing environments (not shown), third party service providers (not shown), network attached storage (NAS) and storage area networks (SAN) to realize application/data transactions.

IV. Kits

Bundling all devices, tools, components, materials, and accessories needed to use a spectroscopic device to test a sample into a kit may enhance the usability and convenience of the devices. Kits can be configured to include, for example, an electromagnetic radiation source for emitting electromagnetic radiation, and a detector adapted to detect photon arrivals and further adapted to detect a delay between the arrival of photons; an autocorrelator adapted to analyze the delay between photon arrivals; and/or one or more filters. The sensors can be disposable or reusable. Additional components can include, for example, alcohol swabs used to clean a surface where a measurement will be taken, prep material to be applied toward a surface where a measurement will be taken to enhance transmission of electromagnetic radiation and the like.

V. Examples

Example 1

Detection of Glucose Levels in Human Tissue

The devices, systems, methods and kits disclosed herein can, for example, be uses to detect levels of glucose in human tissue. The skin surface of a patient can be placed in the system and then radiated with the electromagnetic radiation beam. The beam is reflected out of the skin and carries with it correlations that are representative of wavelengths and absorptions indicative of the blood glucose level in the user. The signal at the detector, along with the same signal after passing through a delay line, are input to an autocorrelator which determines the degree of correlation between the two signal paths. The intensity of the correlation as a function of the delay time then creates a time series that can be related to the spectrum through a Fourier transform. The spectrum can then be interpreted using chemometric methods to determine the level of glucose in the skin tissue sample.

Where the samples are tested in, for example, a lab environment and the spectroscopy devices are part of a communication network, the results along with patient identifying information can then be communicated electronically via the network to the patient and/or healthcare practitioner. Where the samples are tested by a patient in a home environment, the results can be sent to the patient's healthcare practitioner or other party (e.g., diabetes care monitor, family care provider, etc.).

REFERENCES

L. Mandel and E. Wolf, Optical Coherence and Quantum Optics, Cambridge University Press, New York, 1995.
M. Born and E. Wolf, Principles of Optics, Cambridge University Press, 1997.
W. H. Steel, Interferometry, Cambridge University Press, 1967.
Girard, Appl. Optics 2, 79 (1963).
J. G. Hirschberg and P. Platz, Appl. Optics 4, 1375.
W. H. Steel, Interferometry, Cambridge University Press, 1967. p. 123.
L. Mandel, Electromagnetic Theory and Antennas, ed. E. C. Jordan, part 2, p. 811, Macmillan, New York (1963).
A. Michelson, Light Waves and Their Uses, University of Chicago Press (1902).
W. H. Steel, Interferometry, Cambridge University Press, 1967. p. 54.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A correlation interferometric spectroscopy device comprising:
    at least one electromagnetic radiation source for exciting a sample with photons, wherein the photons are introduced from the at least one electromagnetic radiation source to the sample without traversing any optical components;
    a plurality of detectors adapted to detect an arrival time of a photon emitted from the at least one electromagnetic radiation source, wherein the plurality of detectors are further adapted to detect a delay between the arrival time of different photons;
    a system clock adapted to associate a time with a signal received from the plurality of detectors; and
    an autocorrelator adapted to analyze the delay between the arrival times of different photons at the plurality of detectors to determine a correlation between paths traveled by different photons.

2. The device of claim 1 wherein the autocorrelator is further adapted to generate a time series using an intensity of the correlation as a function of the delay between the arrival times.

3. The device of claim 1 wherein the correlations between photons are measured using an aliaser.

4. The device of claim 1 further comprising a Raman spectroscopy device.

5. The device of claim 1 further comprising an attenuated total reflectance spectroscopy device.

6. The device of claim 1 further comprising a pericritical reflection spectroscopy device.

7. The device of claim 1 wherein the system clock is further adapted and configured to associate a time with an emission of an electromagnetic radiation from a source.

8. The device of claim 1 wherein the system clock is further adapted and configured to associate a time with a detection of an electromagnetic radiation from a sample.

9. The device of claim 1 further comprising a power source.

10. The device of claim 1 further comprising a communicator adapted and configured to communicate a measurement from at least one of the one or more detectors, an autocorrelator, a computer processing unit, a delay link, and a memory.

11. The device of claim 1 further comprising a housing.

12. A method for determining the spectral properties of a sample comprising:
    emitting electromagnetic radiation from an electromagnetic radiation source;
    associating an emission time with an emission from the electromagnetic radiation source;
    irradiating the sample with the electromagnetic radiation source, wherein photons from the electromagnetic radiation source are introduced to and interact with the sample without traversing any optical components; and
    detecting an arrival time of the photons at a detector, wherein the photons are exiting the sample;
    analyzing a delay time between the emission time and the arrival time to determine a degree of correlation between paths traveled by different photons.

13. The method of claim 12 further comprising the step of generating a time series using an intensity of the correlation as a function of the delay time.

14. A system for detecting spectral properties of a sample comprising:
    an electromagnetic radiation source for exciting a sample with photons, wherein the photons are introduced from the at least one electromagnetic radiation source to the sample without traversing any optical components;
    a detector adapted to detect an arrival time of a photon emitted from the electromagnetic radiation source and further adapted to detect a delay between the arrival time of different photons;
    a system clock adapted to associate a time stamp with a signal received from the detector;
    a delay line adapted to introduce a time delay into the signal; and
    an autocorrelator adapted to analyze the delay between the arrival times of different photons.

15. The system of claim 14 wherein the autocorrelator is further adapted to determine a degree of correlation between paths traveled by different photons.

16. The system of claim 14 wherein the correlations between photons are measured using an aliaser.

17. The system of claim 14 further comprising a Raman spectroscopy device.

18. The system of claim 14 further comprising an attenuated total reflectance spectroscopy device.

19. The system of claim 14 further comprising a pericritical reflection spectroscopy device.

20. The system of claim 14 wherein the system clock is further adapted and configured to associate a time with an emission of an electromagnetic radiation from a source.

21. The system of claim 14 wherein the system clock is further adapted and configured to associate a time with a detection of an electromagnetic radiation from a sample.

22. The system of claim 14 further comprising a power source.

23. The system of claim 14 further comprising a communicator adapted and configured to communicate a measurement from at least one of the one or more detectors, an autocorrelator, a computer processing unit, a delay link, and a memory.

24. The system of claim 14 further comprising a housing.

25. A kit for detecting the spectral properties of a sample comprising:
    an electromagnetic radiation source for emitting and introducing electromagnetic radiation to the sample without traversing any optical components; and
    a detector adapted to detecting photon arrivals and further adapted to detect a delay between the arrival of photons;
    a system clock adapted to associate a time stamp with a signal received from the detector;
    a delay line adapted to introduce a time delay into the signal;
    an autocorrelator adapted to analyze the delay between arrival of different photons.

26. The kit of claim 25 wherein the autocorrelator is further adapted to determine a degree of correlation between paths traveled by different photons.

27. A networked apparatus comprising:
    a memory;
    a processor electrically coupled to the memory;
    a communicator electrically coupled to the processor;
    a display electrically coupled to the processor; and
    a correlation interferometric spectroscopy device electrically coupled to the processor, the correlation interferometric spectroscopy device comprising at least one electromagnetic radiation source for exciting a sample with photons, wherein the photons are introduced from the at least one electromagnetic radiation source to the sample without traversing any optical components, one or more detectors adapted to detect an arrival time of a photon emitted from the at least one electromagnetic radiation source and wherein the one or more detectors are further adapted to detect a delay between the arrival time of different photons; a system clock adapted to associate a time stamp with a signal received from the one or more detectors; and a delay line adapted to introduce a time delay into the signal.

28. A communication system, comprising:
    a system for measuring a characteristic of a sample comprising a correlation interferometric spectroscopy device comprising at least one electromagnetic radiation source for exciting a sample with photons, wherein the photons are introduced from the at least one electromagnetic radiation source to the sample without traversing any optical components, one or more detectors adapted to detect an arrival time of a photon emitted from the at least one electromagnetic radiation source and wherein the one or more detectors are further adapted to detect a delay between the arrival time of different photons; a system clock adapted to associate a time stamp with a signal received from the one or more detectors; and a delay line adapted to introduce a time delay into the signal;
    a server computer system;
    a measurement module on the server computer system for permitting the transmission of a sample measurement from the system for measuring the characteristic of the sample over a network;
    at least one of an API engine connected to at least one of the system for measuring the characteristic of the sample to create a message about the sample measurement and transmit the message over an API integrated network to a recipient having a predetermined recipient user name, an SMS engine connected to at least one of the system for measuring the characteristic of the sample to create an SMS message about the sample measurement and transmit the SMS message over a network to a recipient device having a predetermined sample measurement recipient telephone number, and an email engine connected to at least one of the system for measuring the characteristic of the sample to create an email message about the sample measurement and transmit the email message over the network to a sample measurement recipient email having a predetermined sample measurement recipient email address.

29. The communication system of claim 28, further comprising a storing module on the server computer system for storing the sample measurement on the system for measuring the characteristic of the sample server database.

30. The communication system of claim 29, wherein the system for measuring the characteristic of the sample is connectable to the server computer system over at least one of a mobile phone network and an Internet network, and a browser on the recipient device is used to retrieve an interface on the server computer system.

31. The communication system of claim 29, wherein a plurality of email addresses are held in a system for measuring the characteristic of the sample database and fewer than all the email addresses are individually selectable from the server computer system, the email message being transmitted to at least one sample measurement recipient email having at least one selected email address.

32. The communication system of claim 31, wherein the system for measuring the characteristic of the sample is connectable to the server computer system over the Internet, and a browser on the recipient device is used to retrieve an interface on the server computer system.

33. The communication system of claim 29, wherein a plurality of user names are held in the system for detecting spectral characteristics database and fewer than all the user names are individually selectable from the computer system, the message being transmitted to at least one sample measurement recipient user name via an API.

34. The communication system of claim 33, wherein the recipient device is connectable to the server computer system over the Internet, and a browser on the sample measurement recipient electronic device is used to retrieve an interface on the server computer system.

35. The communication system of claim 29, wherein the recipient device is connected to the server computer system over a cellular phone network.

36. The communication system of claim 35, wherein the recipient device is a sample measurement recipient mobile device.

37. The communication system of claim 36, further comprising: an interface on the server computer system, the interface being retrievable by an application on the sample measurement recipient mobile device.

38. The communication system of claim 29, wherein the SMS sample measurement is received by a message application on the sample measurement recipient mobile device.

39. The communication system of claim 38, wherein a plurality of SMS sample measurements are received for the sample measurement, each by a respective message application on a respective sample measurement recipient mobile device.

40. The communication system of claim 29, wherein the at least one SMS engine receives an SMS response over the cellular phone SMS network from the sample measurement recipient mobile device and stores an SMS response on the server computer system.

41. The communication system of claim 40, wherein a sample measurement recipient phone number ID is transmitted with the SMS sample measurement to the SMS engine and is used by the server computer system to associate the SMS sample measurement with the SMS response.

42. The communication system of claim 29, wherein the server computer system is connectable over a cellular phone network to receive a response from the sample measurement recipient mobile device.

43. The communication system of claim 42, wherein the SMS sample measurement includes a URL that is selectable at the sample measurement recipient mobile device to respond from the sample measurement recipient mobile device to the server computer system, the server computer system utilizing the URL to associate the response with the SMS sample measurement.

44. The communication system of claim 43, further comprising:
a downloadable application residing on the sample measurement recipient mobile device, the downloadable application transmitting the response and a sample measurement recipient phone number ID over the cellular phone network to the server computer system, the server computer system utilizing the sample measurement recipient phone number ID to associate the response with the SMS sample measurement.

45. The communication system of claim 29, further comprising:
a transmissions module that transmits the sample measurement over a network other than the cellular phone SMS network to a sample measurement recipient user computer system, in parallel with the sample measurement that is sent over the cellular phone SMS network.

46. The communication system of claim 29 further comprising a downloadable application residing on the sample measurement recipient host computer, the downloadable application transmitting a response and a sample measurement recipient phone number ID over the cellular phone network to the server computer system, the server computer system utilizing the sample measurement recipient phone number ID to associate the response with the SMS sample measurement.

* * * * *